United States Patent
Mohr et al.

(10) Patent No.: US 11,211,168 B2
(45) Date of Patent: Dec. 28, 2021

(54) SYSTEMS AND METHODS FOR IDENTIFYING CONTENT BASED ON USER INTERACTIONS

(71) Applicant: NORTHWESTERN UNIVERSITY, Evanston, IL (US)

(72) Inventors: David C. Mohr, Evanston, IL (US); Christopher Karr, Chicago, IL (US)

(73) Assignee: Northwestern University, Evanston, IL (US)

( * ) Notice: Subject to any disclaimer, the term of this patent is extended or adjusted under 35 U.S.C. 154(b) by 784 days.

(21) Appl. No.: 15/654,245

(22) Filed: Jul. 19, 2017

(65) Prior Publication Data
US 2018/0025124 A1 Jan. 25, 2018

Related U.S. Application Data

(60) Provisional application No. 62/364,198, filed on Jul. 19, 2016.

(51) Int. Cl.
*G16H 50/30* (2018.01)
*G06N 20/00* (2019.01)
*H04L 29/08* (2006.01)
*G06F 3/048* (2013.01)
*G06N 5/02* (2006.01)

(52) U.S. Cl.
CPC ............. *G16H 50/30* (2018.01); *G06F 3/048* (2013.01); *G06N 20/00* (2019.01); *H04L 67/22* (2013.01); *G06N 5/02* (2013.01)

(58) Field of Classification Search
CPC ......... G16H 50/30; G06F 3/048; H04L 67/22; G06N 5/02; G06N 20/00
See application file for complete search history.

(56) References Cited

U.S. PATENT DOCUMENTS

| | | | | |
|---|---|---|---|---|
| 2012/0084292 | A1* | 4/2012 | Liang | G06F 16/2228 707/741 |
| 2014/0052683 | A1* | 2/2014 | Kirkham | G06N 5/04 706/46 |
| 2017/0220782 | A1* | 8/2017 | Alsanousi | G06F 21/126 |

* cited by examiner

*Primary Examiner* — Michael Tomaszewski
*Assistant Examiner* — Mohmad Muqueeth
(74) *Attorney, Agent, or Firm* — Banner & Witcoff, Ltd.

(57) ABSTRACT

Disclosed is an intelligent recommendation system for identifying and/or providing personalized one or more independent applications and/or healthcare related media content (e.g., multimedia content and applications involved in healthcare or the treatment of various health conditions of a user) to a plurality of user devices and/or client devices.

21 Claims, 4 Drawing Sheets

SYSTEMS AND METHODS FOR IDENTIFYING CONTENT BASED ON USER INTERACTIONS

CROSS REFERENCE TO RELATED APPLICATION

The present non-provisional utility application claims priority under 35 U.S.C. § 119(e) to provisional application No. 62/364,198 entitled "Systems And Methods For Identifying Content Based On User Interactions," filed on Jul. 19, 2016, and which is hereby incorporated by reference herein.

STATEMENT REGARDING FEDERALLY SPONSORED RESEARCH OR DEVELOPMENT

This invention was made with government support under R01 MH100482 awarded by the National Institutes of Health. The government has certain rights in the invention.

TECHNICAL FIELD

Aspects of the present disclosure relate to computing devices and hardware used in data aggregation and processing, particularly regarding healthcare related-data, applications, and information.

BACKGROUND

The majority of health care providers offer services, prescriptions, treatment regiments, advice, etc., to patients on a continuing basis. As patients grow older, develop chronic conditions, and/or fall ill to serious health conditions, they typically will require more frequent and continuous access to doctors, prescription medicine, hospitals, etc. For example, a patient suffering from chronic anxiety or diabetes may require continuous interactions with medical providers and/or other health related services in order to ensure the patient can properly manage the various symptoms associated with his/her condition.

Mobile phones and other remote digital devices have become a popular mechanism to provide health care related treatments and services to patients suffering from chronic conditions, as such devices may be used on a daily basis to allow a user to engage in a variety of different medical-related tasks and access a variety of healthcare related content and applications. Moreover, the widespread use of mobile devices makes effective therapies accessible to large numbers of users. Ensuring users have access to useful and clinically meaningful content and applications may present challenges.

BRIEF DESCRIPTION OF THE DRAWINGS

The foregoing and other objects, features, and advantages of the present disclosure set forth herein will be apparent from the following description of particular embodiments of those inventive concepts, as illustrated in the accompanying drawings. Also, in the drawings the like reference characters refer to the same parts throughout the different views. The drawings depict only typical embodiments of the present disclosure and, therefore, are not to be considered limiting in scope.

DETAILED DESCRIPTION

Aspects of the present disclosure involve an intelligent recommendation system that automatically generates a recommendation of one or more independent applications (e.g., applets or modules) for inclusion into a platform of applications currently being executed or otherwise provided at one or user devices and/or client devices. In various embodiments, the intelligent recommendation system includes a searching and matching utility that automatically identifies a series of independent applications for execution at the user devices/client devices, based on a health profile of a user, health conditions of the user, treatments prescribed to the user, known health risk factors corresponding to the user, behaviors of the user when engaged in medical treatment, as well as similarities with other users having similar patterns corresponding to the user's health profile and overall health conditions and environment (e.g., employing machine-learning algorithms trained using data corresponding to a large pool of users having similar patterns). In one specific example, the independent applications identified by the intelligent recommendation system may relate to a specific medical condition of a patient, such as anxiety, depression, obesity, and/or the like. Thus, rather than implementing a "one-size" fits all strategy wherein a single, large and complex application, is provided to users dealing with a particular health concern or condition, the intelligent recommendation system automatically identifies a suite of applications for the user that targets specific aspects of the health concern or condition, thereby offering more meaningful and engaging treatment to the user.

In some embodiments, the independent applications identified by the system and provided to a user at a client device may be automatically identified based on past user engagement or user interactions with other independent applications currently being provided at the user devices and/or client devices. For example, a new application may be identified for a particular user based on the user's interaction or engagement with previous applications, or previous versions of applications, provided to the user by the intelligent recommendation system and currently executing at the user device and/or client device. In other embodiments, data may be captured from various sensors coupled to or in communication with the user devices and/or client devices that provide information about health conditions of the user. For example, bio-inspired structures that incorporate a sensing element and polymer may be coupled to or in communication with the user devices and/or client devices, such as a patient position sensor (accelerometer), Glucometer Sensor, Body Temperature Sensor, Blood Pressure Sensor (Sphygmomanometer), Pulse and Oxygen in Blood Sensor (SPO2), Airflow Sensor (Breathing), Galvanic Skin Response Sensor (GSR—Sweating), Electrocardiogram Sensor (ECG), and/or biometric sensors, among others. Any of such sensors can be desirable in evaluating a number of medical conditions of a user and such sensors may communicate with the user devices and/or client devices to provide data concerning the user's heath and/or health conditions.

By automatically generating recommendations of new applications and/or content based on past user interactions, the system can ensures that the user is receiving fine-tuned and specific healthcare treatments in real-time, without human intervention of a doctor, therapist, etc.

Accordingly, the intelligent recommendation system may be dynamically driven by historic and/or real-time interactions and related data generated by a user interacting with the applications currently being provided or previously provided by the intelligent recommendation system. The intelligent recommendation system can function without large amounts of data entry setup from a user, such as requiring a user to complete ongoing self-reporting questionnaires. Rather, the intelligent recommendation system automatically monitors user interactions with an initial application (or set of applications), automatically determines whether the user interactions are indicative of a positive clinical response to the initial application, and recommends other applications based on the positive clinical response data (determined from the user interactions, as will be described below). Thus, the intelligent recommendation system automatically identifies and provides users with additional applications that enable the users to stay updated, in real-time, on relevant health issues and health interests.

In other aspects, the independent applications may be provided and/or otherwise delivered to the user devices via a software container, web portal, dashboard, platform, graphical user-interface, and/or the like. More specifically, the heath content and/or independent applications may be integrated into a single, cloud-based, cross-platform, and/or distributed application that enable users, regardless of their computing device and platform, to access applicable the applications (or related content). For example, a web-based version of a platform may be provided, enabling the loading of its components within a browser or other network-based environment. Various execution environments are possible and may include a browser application. Examples of browser applications include but are not limited to desktop versions of browsers, mobile browser applications, browser applications, or functionality that may be integrated with an operating system, or any other variation or combination of browser. In such a scenario, the information management application may be a browser-based application and its various components may load from a browser cache. One benefit of loading all of the components of an application into a recommendation environment or platform is that, once all of the components are loaded, interaction with any given aspect of the application may be fast and responsive.

In yet other aspects, the identified set of applications may be loaded into a larger, integrated application or platform, based at least in part on user interactions with related applications or historic applications involving the health of the user. In one specific example, the applications may be provided as a suite of applications containing individual applications that have been validated to address (e.g., treat) various health conditions of the user. Generally speaking, a software suite or application suite is a collection of computer programs—usually application software or programming software—of related functionality, often sharing a similar user interface (e.g., a graphical user-interface) and the ability to easily exchange data with each other.

A series of illustrative examples of the type of individual applications and/or healthcare media content that may be integrated into a platform and/or suite of applications will now be provided. It is contemplated, however, that other individual applications may be identified and recommended.

Aspire Application: Aspire provides the tools to help users select positive values that the user wishes to enact in their everyday lives. The user begins by selecting several values to focus on, and the application provides suggested "paths" which the user may complete to enact that value. The application uses a daily reminder to keep the user engaged throughout the lifetime of the application.

BOOST ME Application: Boost Me is an application that can provide positive activities that have worked for an individual patient in the past or gives him or her suggestions, based on how he or she is feeling. Patients who notice an improvement in your mood can log what they did in Boost Me to have a reminder in the future of something that made them feel better. Boost Me encourages users to schedule activities in the future that will help improve their mood. During the set up process, the user is prompted to choose an activity, a time to do it, and their predicted mood after the activity. The application integrates with the system calendar to help integrate the "boost" into their daily life. After the "boost" is completed, the user rates their actual mood and this feedback helps the user learn to choose mood boosting activities in the future.

Daily Feats Application: Daily Feats provides users with a calendar for keeping track of the things that they accomplish each day. The application encourages the user to complete streaks of days where they both complete and log their achievements for that day in order to motivate action and allow the user to recognize their achievements. The application includes various "levels" of actions, from basic tasks for severely depressed users to more ambitious tasks for less afflicted users. As the user completes streaks spanning several days, they "level up" and are encouraged to achieve more ambitious goals over time.

iCope Application: iCope automatically transmits inspirational messages and reassuring statements to users. iCope encourages the user to anticipate situations in the future where they may need a reminder or tip to help out. The application implements the coping card strategy where the user designs and schedules coping cards to be delivered when they need them.

MoveMe Application: MoveMe provides tools to help the user schedule and complete short physical exercises that are selected to help the user improve their mood. It integrates with the local calendar so that the scheduled movement exercises become part of the user's daily life. It also includes links to resources and examples of suitable physical exercises that the user can choose complete.

My Mantra Application: My Mantra implements a mantra-based strategy for improving mood by providing a visual experience that allows the user to associate mantras that they can repeat with photos, illustrations, and other images that reinforce the mantra's message. The application uses a notification strategy coupled with the user-selected imagery to encourage the user recite their mantras regularly.

Purple Chill Application: Purple Chill is a repository of audio relaxation exercises to help the user relax and relieve stress throughout the day. The application includes several different content sections containing multiple tracks each. It uses a built-in media player provide consistent access to the audio content within the application, as well as a notification that encourages the user to complete a relaxation exercise at least daily. In addition to the content, the application also prompts the user to rate their stress before and after listening to the track so that effective tracks can be easily highlighted for future sessions.

Slumber Time Application: Slumber Time provides a suite of tools to help users engage in better sleeping practices and to understand what may be negatively affecting their nightly slumbers. The application includes a variety of tools, including a reference section with educational content, a bedtime checklist to help users complete a nightly ritual before going to bed, and a built-in alarm clock that monitors the environment for potential light-or sound-based disruptions. The application encourages the user to track their sleep in an interactive diary that provides suggestions about best practices as the user describes their sleep.

Social Force Application: Social Force helps users identify their positive support network and provides reminders and tools to help them get in touch regularly with their supporters. The application interviews the user to identify their supporters and integrates with the device's calling and text features to display how often contact occurs as well as providing direct links to the local phone and texting features to make reaching out quick and easy.

Thought Challenger Application: Thought Challenger implements a negative thought challenging exercise that teaches users how to counter automatic negative thoughts with an application appropriate response to prevent those automatic thoughts from negatively impacting the user's mood.

Worry Knot Application: Worry Knot is an application that implements exercises to help users break out of the process of ruminating on negative thoughts by using neutral thoughts to counter the effect of the negative thinking.

Although the present application refers to generating recommendation including independent applications, it is contemplated that other types of content that may be identified and included in a recommendation generated by the system, based on user interactions, such as healthcare related media content (e.g., video, audio, images), and of which may be used during the treatment of various health conditions of a user.

Figure 1:
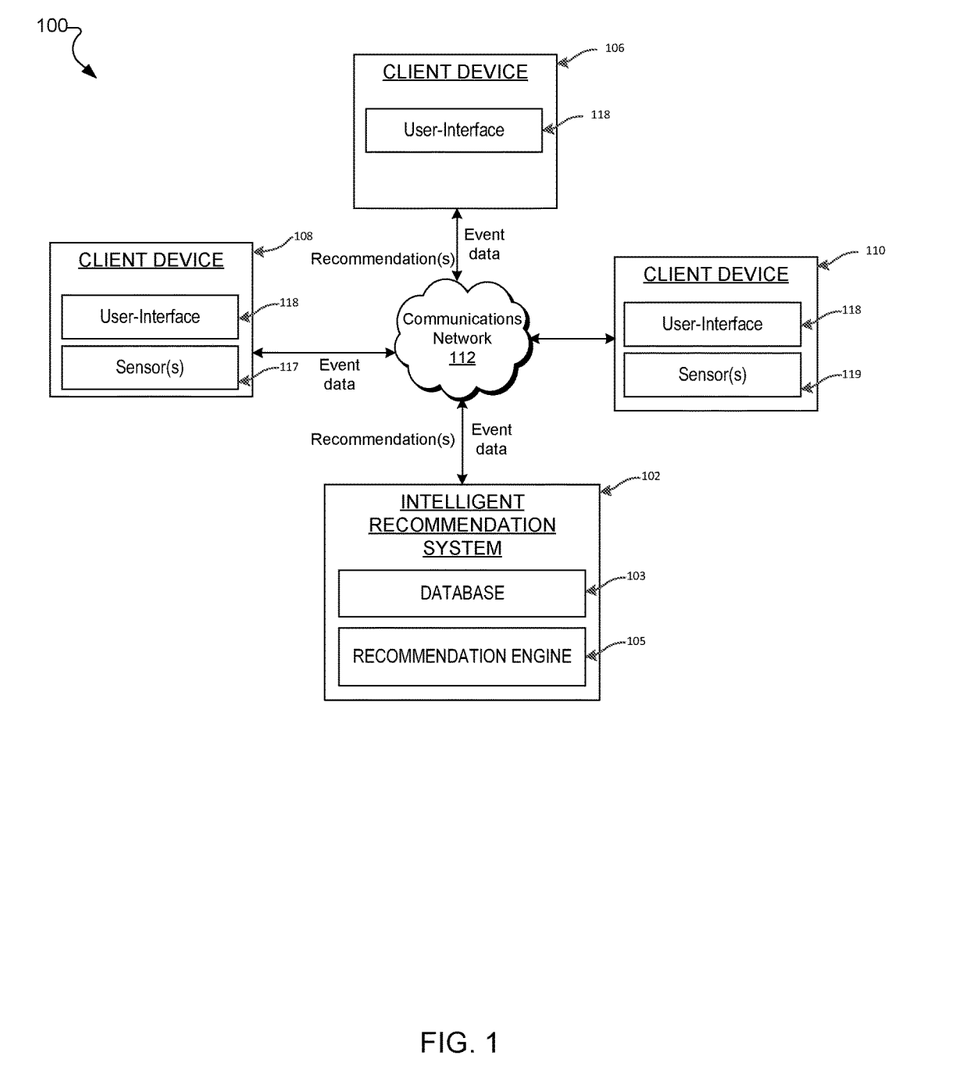
FIG. 1 is a block diagram illustrating a computing architecture for generating recommendations of individual applications and/or healthcare related content, based on user interactions, according to aspects of the present disclosure.

FIG. 1 illustrates one example of a computing architecture 100 for automatically generating a recommendation of one or more individual applications for integration into a platform of applications currently being used by a user to treat a medical condition, according to one embodiment. Generally, the computing architecture 100 includes various devices functioning together in the gathering, transmitting, requesting, and/or manipulation of applications and data being used to clinically treat one or more health conditions of a user, or more generally the health of a user. In the illustrated embodiment, the computing architecture 100 includes an intelligent recommendation system 102 that includes a mechanism for identifying one or more individual applications (or modules) that may be provided to one or more user devices and/or client devices for execution and user access.

As further illustrated, the intelligent recommendation system 102 includes a database and/or data store 103 (or some other database architecture including those embodied in a single database or multiple databases of the same or differing platforms) that is used to store, among other information and content, data relating to heath care content and/or health-care related applications, and in particular user interactions and event data generated from users interacting with a current set of applications provided by the intelligent recommendation system to a user device and/or client device. For example, the event data may include raw data and information illustrating how a user interacted with and reacted to a series of independent applications related to a specific aspect of treatment for a medical condition corresponding to the user, such as anxiety. In another example, the event data may include raw data articulating how a user interacted with one or more independent applications related to a specific aspect of treatment for a medical condition, such as depression. It is contemplated that the current set of applications provided by the intelligent recommendation system may involve any application or content that is scientifically validated to address and/or treat any type of chronic medical condition.

The intelligent recommendation system 102 further includes a recommendation engine 105 that processes the event data (and in some embodiments, the healthcare data) to identify healthcare media content and/or applications for presentation to a user. More specifically, the recommendation engine 105 generates one or more recommendations based on a user's interaction (e.g., the stored event data) with other healthcare media content and/or independent applications previously provided by the intelligent recommendation system 102. For example, the recommendation engine 105 may generate a recommendation indicating that an application "A" should be provided to a user, based on the user's current and/or previous interactions (i.e., articulated by the event data) with applications B and C. In other embodiments, the recommendation engine 105 may process other information about the user and his/her interaction with the user device and/or client device, such as its current location and movement history (e.g., continuous geo-location), its texting behaviors, e-mail communications, and/or the like.

One or more client devices 106-110 functionally communicate with the intelligent recommendation system 102 through a communications network 112, which may be the Internet, an intranet, and Ethernet network, a wireline network, a wireless network, and/or another communication network. The one or more client devices 106-110 may be a personal computer, work station, mobile device, mobile phone, tablet device, processor, and/or other processing device capable of implementing and/or executing processes, software, applications, etc., that includes network-enabled devices and/or software, such as a user-interface 118 for communication over the communications network 112 (e.g., browsing the internet). Additionally, the one or more client device(s) 106-110 may include one or more processors that process software or other machine-readable instructions and may include a memory to store the software or other machine-readable instructions and data. In one specific example, the client device may include one or more sensors 117 119. For example, the sensors 117 and 119 may be configured to capture biometric data associated with a user. Biometric data describes one or more physical traits of a user of the client device 110 capable of uniquely identifying the user. Alternatively, the sensors 117 and 119 may be used to capture other data associated with various health conditions of a user.

Figure 2:
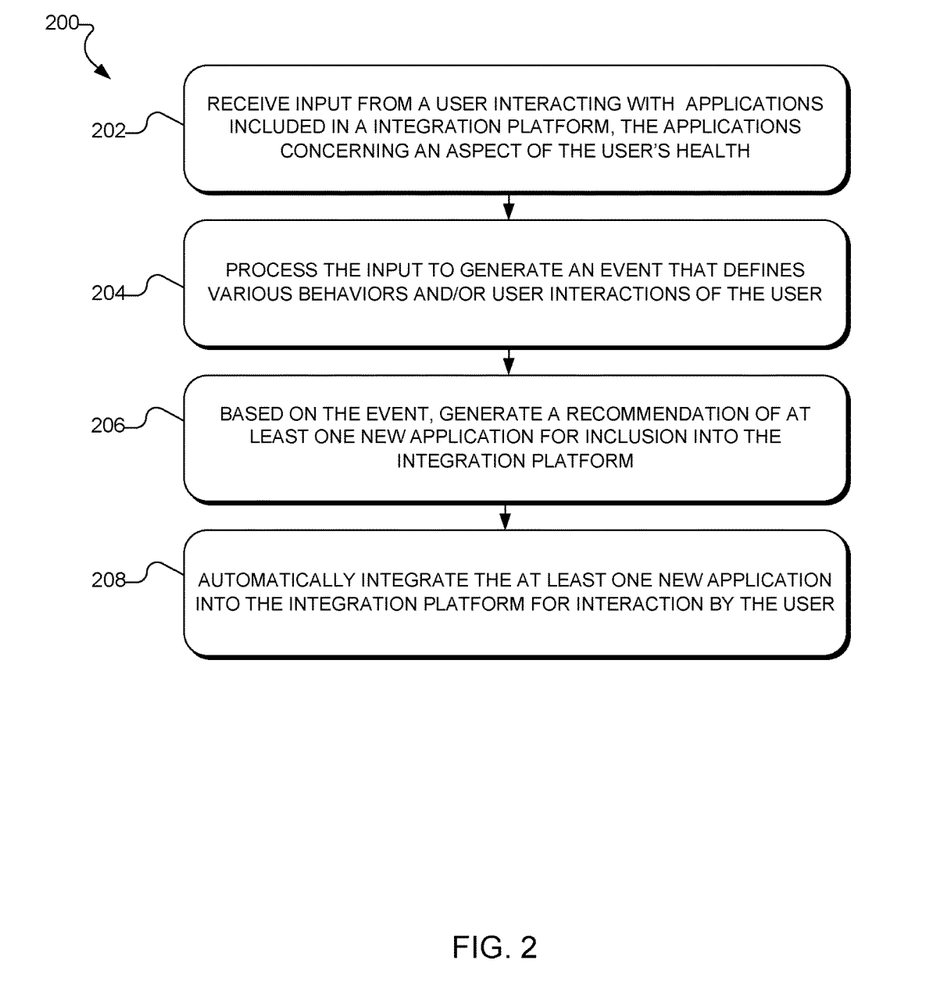
FIG. 2 is a flowchart of an example recommendation generation process, according to aspects of the present disclosure.

Referring now to FIG. 2 and with reference to FIG. 1, an illustrative process 200 for generating recommendations of new healthcare media content and/or applications with which a user may interact to treat a particular media condition is provided. Referring initially to FIG. 2, process 200 begins with receiving or otherwise obtaining user interactions corresponding to a user interacting with an initial set (may be only one) of applications (or other healthcare related media content) that concern some aspect of the user's health, or specific health condition of the user (operation 202). In one example and with reference to FIG. 1, the intelligent recommendation system 102 may generate an interactive platform (e.g. a user-interface or graphical user-interface (GUI)) that includes interactive elements, such as buttons, forms, activity logs, fields, streaming capabilities, selections, inputs, streams, images, etc., charts, for displaying the recommended healthcare media content and/or the recommended applications. For example, in one specific example, the platform may include one or more independent applications that correspond to some aspect of some type of treatment or care for some health concern of the user.

The generated platform may be provided to one of the client devices 106-110 for display and execution. A user may interact with the one or more client devices 106-110 and interact with the applications and thereby provide input that defines the behavior of the user when receiving such treatment. All of such input is stored in the database of the intelligent recommendation system 102 for later analysis when generating recommendations of additional applications (or other healthcare media content) for inclusion into the platform. Thus, the intelligent recommendation system 102 monitors user interaction with respect to the platform and the one or more individual applications included in the platform. For example, the intelligent recommendation system 102 may monitor which individual applications included in the platform a user may interact with the most. In another example, the information exchange service may monitor with which individual applications of the various individual applications included in the platform that a user tends to interact with first (or the most) relative to the other individual applications, during an initial period of time, such as during a particular period of medical treatment.

Referring again to FIG. 2, the obtained user-interactions and input is processed to generate and/or otherwise extract one or more events that define or otherwise capture various behaviors and interactions of the user (operation 204). Referring to FIG. 1, initially, the intelligent recommendation system 102 may receive the user interactions from the client devices 106-110 and process the input to extract events and remove any duplicates. Each application accessible by a user within the platform may include logging instructions such as:

```
final HashMap<String, Object> payload = new HashMap< >( );
...
payload.put("mantra_title", title);
...
LogManager.getInstance(this).log("opened_mantra", payload);
```

The logging instructions construct or otherwise encapsulate an event that is saved to a database. Events are attached to whatever interactions that the user has within a given application and/or healthcare media content. Such interactions may include opening particular media files, content and/or pages (e.g., web pages), completing exercises within a given application, and responding to notifications. Periodically, an application may determine if a network connection is available, and if so, it transmit the accumulated events to the intelligent recommendation system.

In some embodiments, the intelligent recommendation system may attach additional information to the event to assist in identifying the user who generated the event. Other metadata may also be attached to the event that describes and identifies the platform in which the application is running for troubleshooting purposes.

In one embodiment, when the event is stored at the intelligent recommendation system, it may be encoded using JSON:

```
{
"mantra_title": "I am resilient",
"event_type": "opened_mantra",
"package": "edu.xxxxxxxxxxx.cbits.intellicare.mantra",
"timestamp": 1466518910,
"version_code": 10043,
"os_version": "5.0.1",
"version": "1.0.43",
"user_id": "0954ce41093679c6c7fb3454f3ad06b4",
"model": "SCH-I545",
"os": "android",
"manufacturer": "samsung"
}
```

Using a JSON-based format like this allows for the generation of custom event types without the need for coordinating schemas with the intelligent recommendation system 102. In the JSON example above, the user_id element is a hexadecimal string encoding an MD5 hash of the user's local identifier (typically an email address) salted with a shared secret to generate the hash. The use of the one-way MD5 function protects the user's identity from disclosure outside the intelligent recommendation system 102. Any of the events may be aggregated to create a stream of events.

Referring again to FIG. 2, the events (or stream of events) may be processed to identify one or more user features, which may be used to generate a predictive model for enabling the intelligent recommendation system to generate recommendations identifying individual applications that maximize user engagement. Stated differently, the intelligent recommendation system may generate a model representing the event data as a function of the values of the identified features. Moreover, in some embodiments, the intelligent recommendation system 102 may employ various machine learning methodologies to automatically and continuously learn and re-learn to analyze the event data, which may be processed by the intelligent recommendation system to generate more accurate application recommendations. Generally speaking, machine learning represents a form of computing in which artificial intelligence is employed to allow computers to evolve behaviors based on empirical data (e.g., event data and features extracted from event data). Machine learning may take advantage of training examples to capture characteristics of interest of its unknown underlying probability distribution.

Figure 3:
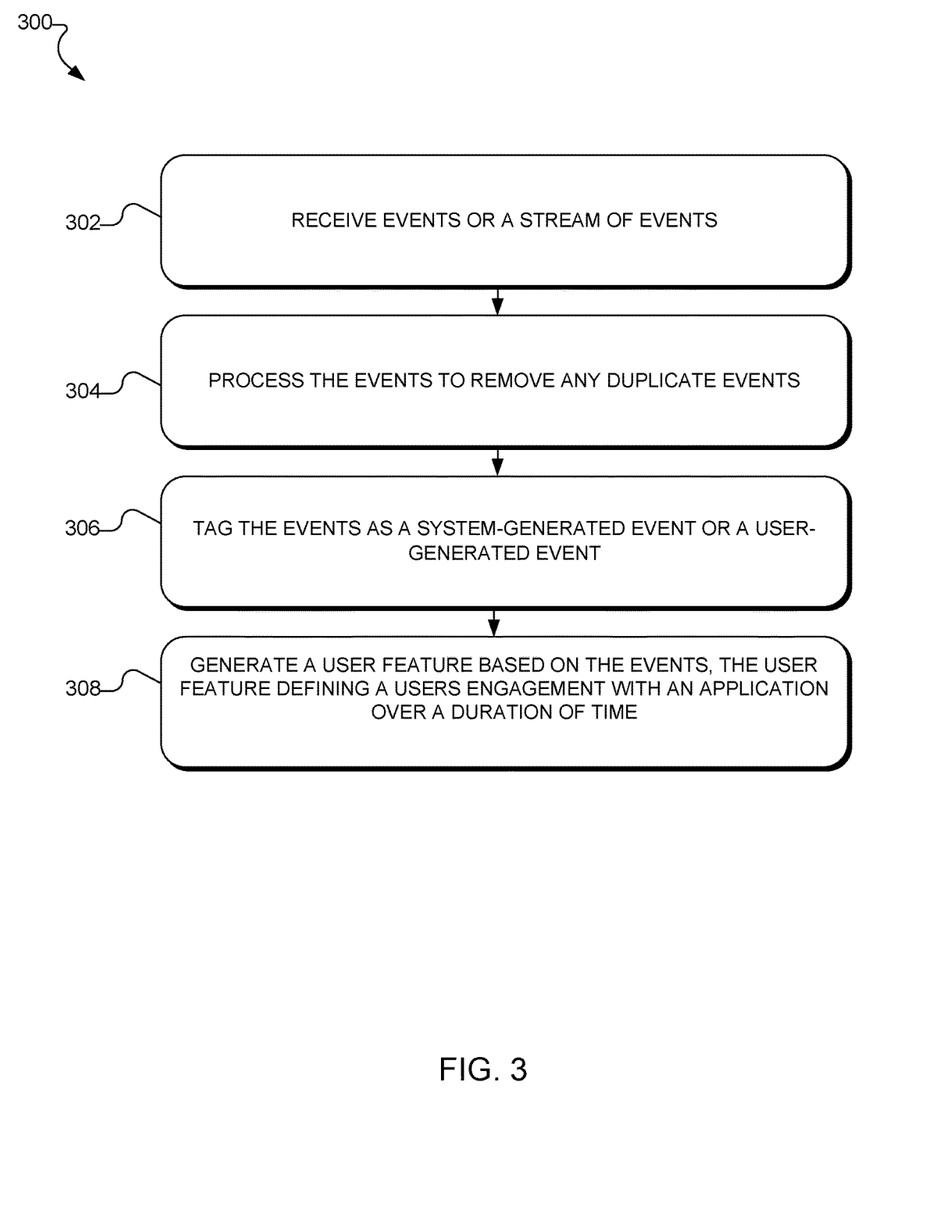
FIG. 3 is a flowchart of an example user feature extraction process, according to aspects of the present disclosure.

Feature selection identifies and removes unneeded, irrelevant, and redundant data from the events so that such data do not contribute to the accuracy of the recommendation engine of the intelligent recommendation system. FIG. 3 provides an illustration of a process 300 for identifying user features from events, according to one embodiment. As illustrated, process 300 begins with the intelligent recommendation system receiving an event, or a stream of events (operation 302). The intelligent recommendation system inspects the events and removes any duplicates that may have been transmitted by a programming or network error (operation 304). Additionally, the intelligent recommendation system may tag the event as user- or system-generated (operation 306).

Periodically, (e.g., once a week, day, or hour), for each user (the exact time determined by user's first use of the initial applications), the intelligent recommendation system 102 generates a user "feature" object that contains a condensed version of the user's engagement with each application over a duration of time, such as a week, month or year (operation 308). In one specific example, the following algorithm may be executed to extract features:

1. Generate a list of all user-application pairs where at least one event has been generated.
2. For each pair, fetch the events for the pair from the last year.
3. For each date in the event timeline, create an accumulator that will log the number of daily sessions for from the start of engagement to the end of engagement.
4. For event in the event timeline:
   a. Determine if the current event is part of an existing session or start of a new application session.
      i. A session is defined as a sequence of user-generated events that occur less than 5 minutes apart, or some other pre-defined time period.
      ii. If an event begins a new session, increment the count of the daily session count accumulator.
   b. Translate the event object into a substring that will be used to detect clinically-meaningful patterns.
      i. Example of an Aspire application session translated into a string: Om . . . Om.Om . . . CcCcCcCcCc . . . CcOm . . . SpSpSp . . .
         1. Om=Opened main screen.
         2. Cc=Closed select values screen.
         3. Sp=Selected path (completed item).
         4 . . . =Event not used to calculate clinical engagement.
   c. From the session string, calculate the number of clinically-meaningful sequences encountered.
      i. Sequences are detected by applying a regular expression pattern for each clinically-meaningful use and counting the number of occurrences in the session string.
         1. Example: "Read four pages of help content"=OspSpSpSpSp
            a. Osp=Opened Help screen.
            b. Sp=Advanced a page.
         2. Example (single event): "Added a path"=Ap
   d. From the event timestamps, calculate the following descriptives:
      i. Date of first use.
      ii. Date of last use.
      iii. Number of time rated the application.
      iv. Average number of sessions per day (if used more than one day).
      v. Average session time.
      vi. Total usage duration (last use—first use)
   e. Cache calculated quantities.

At the conclusion, each user has a saved report and/or data object that contains the following content:

```
{
"edu.xxxxxxxxxx.cbits.intellicare.moveme": { },
"edu. xxxxxxxxxx.cbits.intellicare.boostme": { },
"edu. xxxxxxxxxx.cbits.intellicare.aspire": {
   "num_sessions": 1,
   "total_session_time": 131.0,
   "event_sequence": "Om....Om.Om..CcCcCcCcCc..CcOm..SpSpSp...",
   "interactions": {
      "help_-Four": 0,
      "opened_main": 4,
      "Fetched_photo": 0,
      "closed_cards": 6,
      "edited_value": 0,
      "sequence_read_-Faq": 0,
      "deleted_path": 0,
      "selected_path": 3,
      "renamed_path": 0,
      "added_path": 0
   },
   "last_use": "2016-03-22T03:05:49+00:00",
```

-continued

```
   "-First_use": "2016-03-22T03:03:38+00:00",
   "num_ratings": 0,
   "sessions_per_day": 0,
   "total_use_duration": 0.0015162037037037036,
   "mean_session_time": 131.0
},
"edu. xxxxxxxxxx.cbits.intellicare.social-Force": { },
"edu. xxxxxxxxxx.cbits.intellicare.icope": { },
"edu. xxxxxxxxxx.cbits.intellicare.daily-Feats": { },
"edu. xxxxxxxxxx.cbits.intellicare.worryknot": { },
"edu. xxxxxxxxxx.cbits.intellicare.messages": { },
"edu. xxxxxxxxxx.cbits.intellicare.thoughtchallenger": { },
"edu. xxxxxxxxxx.cbits.intellicare.relax": { },
"edu. xxxxxxxxxx.cbits.intellicare.conductor": { },
"edu. xxxxxxxxxx.cbits.intellicare.slumbertime": { },
"edu. xxxxxxxxxx.cbits.intellicare.mantra": { },
"edu. xxxxxxxxxx.cbits.intellicare.melocate": { }
}
```

In the example above, the user only used Aspire, and only used it once for a little over 2 minutes. During that single session, the user completed the clinical goals of opening the main screen, reviewing virtues, and selecting paths.

Referring again to FIG. 2, the events (e.g., one event or several events) and/or the user feature objects are processed to generate recommendations identifying a set of individual applications (or healthcare related media content components) for inclusion into the platform (operation 206). Referring to FIG. 1, the recommendation engine 105 of the intelligent recommendation system 102 predicts and/or matches new applications for inclusion into the integration platform based on the events and/or user feature objects.

In one embodiment, recommendation engine 105 may aggregate feature objects into a pool of engagements for each user-application pair. The counts of meaningful clinical event counts are normalized to a value between 0 and 1 to account for differences in the ranges of meaningful clinical action options between applications.

Then for each user, the normalized clinical counts are used to generate a new set of features that describe which application in every pair is the "winner" of the comparison of clinical engagements on a per-user basis. For example, given a user that has used the following applications, with each's normalized clinical engagement score:
Aspire: 0.90
MoveMe: 0.70
My Mantra: 0.20
Social Force: 0.95
The process would produce the following features for the user:
Aspire-v-MoveMe: 1
Aspire-v-MyMantra: 1
Aspire-v-SocialForce: 0
MoveMe-v-MyMantra: 1
MoveMe-v-SocialForce: 0
MyMantra-v-SocialForce: 0
This is effectively generating the outcomes of head-to-head matchups between the applications where the winner is determined by the largest clinical engagement score.

These are used to generate a data set where each example corresponds with a user and the features in that example are the outcome of the application-vs-application matches above.

The next step generates the application predictions for each user. Given the example set above, a k-Nearest-Neighbors model (or other type of pattern recognition model) may be used to predict the outcome of match-ups between the applications, using the existing comparisons (between applications that the user has already used) as training input to the model.

For each application that has not yet been used, the model generates binary predictions of which application will "win" in the contest to produce higher clinical engagement. The output of this phase will be of the form:

PurpleChill-v-ThoughtChallenger: 1
PurpleChill-v-WorryKnot: 1
PurpleChill-SlumberTime: 0
ThoughtChallenger-v-WorryKnot: 1
ThoughtChallenger-v-SlumberTime: 0
WorryKnot-v-SlumberTime: 0

The prediction model will generate pair-wise predictions that identify which application or applications will generate more clinically-meaningful use. To rank the recommendations, the system uses a TrueSkill ranking algorithm (or other ranking algorithm) to transform the "win/loss" records into a ranked list with the strongest unused application on top. Applications that have already been used are placed at the bottom of the list with a ranking score of 0. These rankings are cached for retrieval by the device in the form:

```
{
"edu.xxxxxxxxxx.cbits.intellicare.social-Force": {
"reason": "Recommended by ranking algorithm.",
"score": 0.5687932615869578,
"application": "edu. xxxxxxxxxx.cbits.intellicare.social-Force"
},
"edu. xxxxxxxxxx.cbits.intellicare.boostme": {
"reason": "Recommended by ranking algorithm.",
"score": 8.851320943114997,
"application": "edu. xxxxxxxxxx.cbits.intellicare.boostme"
},
...
}
```

The device sorts the list by score and the top one becomes the recommendation. In the example above, BoostMe is a much stronger recommendation than Social Force. Thus, rather than try to predict the expected clinical engagement and use that directly as a recommendation score (i.e. "How much engagement can I expect if X is recommended?", a continuous value), the approach above predicts which application will produce a higher clinical engagement when compared against an alternative (i.e. "Will X produce higher clinical engagement than Y?"—a binary value).

Referring again to FIG. 2, based on the generated recommendations, new relevant independent applications are provided or otherwise integrated into the platform and displayed at a user device/client device for user interaction (operation 208). Referring to FIG. 1, the intelligent recommendation system 102 automatically integrates or otherwise loads the recommended applications into the integration platform for execution and interaction by a user. For instance, the components may be loaded from a remote source, such as a server associated with the intelligent recommendation system 102. Once the individual applications are loaded, the individual applications can be executed within the context of the platform running in the browser application.

Alternatively, one or more notifications may be provided to the applicable user device to indicate to a user that new applications have been identified for use. In some embodiments, the applications may be prioritized based on a level of relevance to the user. For example, the intelligent recommendation system 102 may determine that a particular application is more relevant than another, based on a frequency of use by a user or based on the relevance of the content of the application in relation to the user's health condition and provide the application to the integration platform in a prioritized manner.

Thus, intelligent recommendation system consists of a collection of applications where the applications may be independent of each other and attempt to address an element of a specific health condition in a manner orthogonal to other applications in the suite. Applications may be (and have been) added to the suite as new application approaches are implemented and applications may be (and have been) retired from the suite when they do not meet the engagement or clinical standards when released to users. The intelligent recommendation system anticipates and embraces the fluidity of applications entering and exiting the platform and uses a data-driven application approach to combine engagement data from existing applications with the data from the new applications to integrate the additions into the platform smoothly. As users master applications and begin to extract the maximal clinical benefit each application, the intelligent recommendation system provides automated recommendations to assist users in selecting new or additional applications beyond their first application. The recommendations maximize meaningful clinical engagement.

Figure 4:
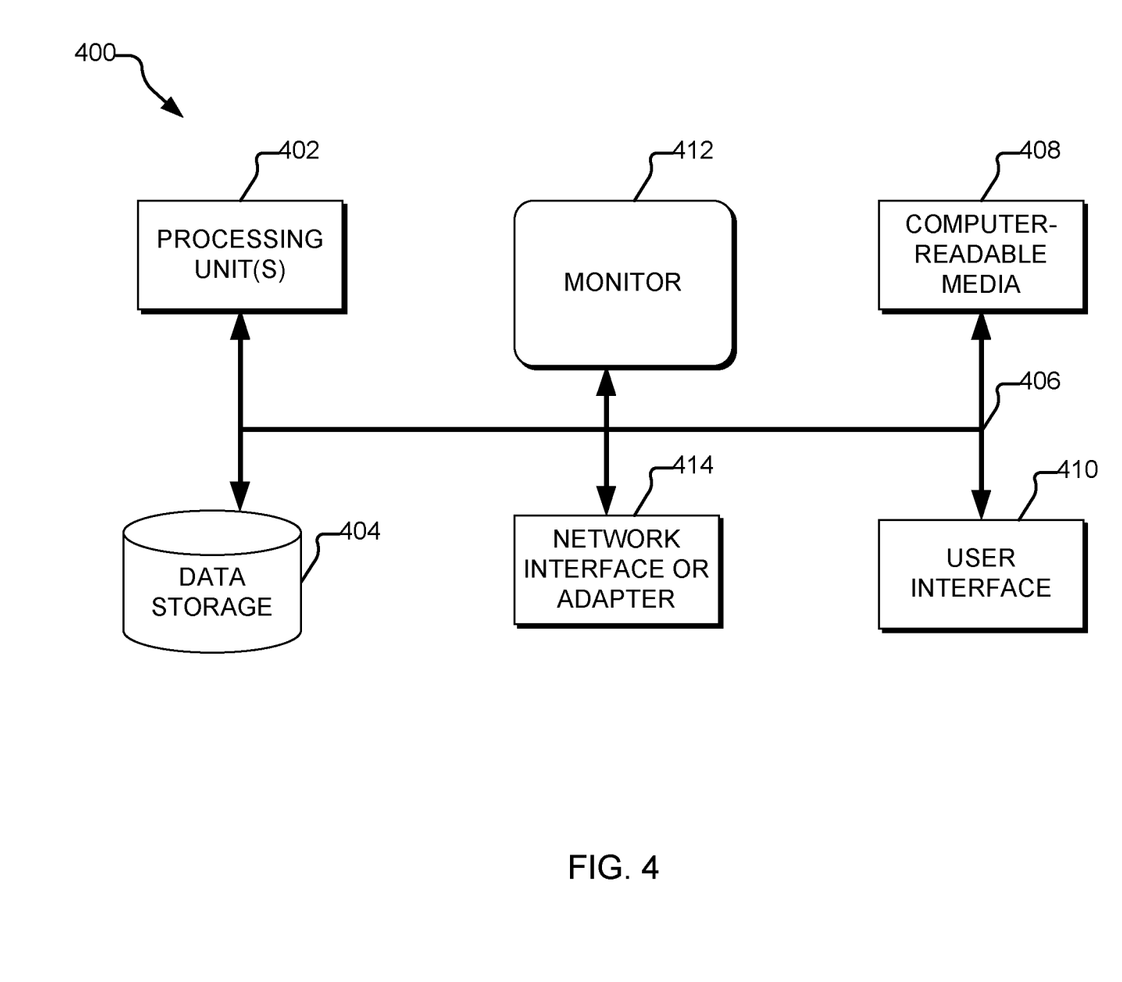
FIG. 4 is a block diagram illustrating a computing device, according to aspects of the present disclosure.

FIG. 4 illustrates an example of a suitable computing and networking environment 400 that may be used to implement various aspects of the present disclosure described in FIGS. 1-2, such as the intelligent recommendation system 102. As illustrated, the computing and networking environment 400 includes a general purpose computing device 400, although it is contemplated that the networking environment 400 may include one or more other computing systems, such as personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments that include any of the above computing systems or devices, and the like.

Components of the computer 400 may include various hardware components, such as a processing unit 402, a data storage 404 (e.g., a system memory), and a system bus 406 that couples various system components of the computer 400 to the processing unit 402. The system bus 406 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computer 400 may further include a variety of computer-readable media 408 that includes removable/non-removable media and volatile/nonvolatile media, but excludes transitory propagated signals. Computer-readable media 408 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/data and which may be accessed by the computer 400. Communication media includes computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The data storage or system memory 404 includes computer storage media in the form of volatile/nonvolatile memory such as read only memory (ROM) and random access memory (RAM). A basic input/output system (BIOS), containing the basic routines that help to transfer information between elements within the computer 400 (e.g., during start-up) is typically stored in ROM. RAM typically contains data and/or program modules that are immediately accessible to and/or presently being operated on by processing unit 402. For example, in one embodiment, data storage 404 holds an operating system, application programs, and other program modules and program data.

Data storage 404 may also include other removable/non-removable, volatile/nonvolatile computer storage media. For example, data storage 404 may be: a hard disk drive that reads from or writes to non-removable, nonvolatile magnetic media; a magnetic disk drive that reads from or writes to a removable, nonvolatile magnetic disk; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media, described above and illustrated in FIG. 4, provide storage of computer-readable instructions, data structures, program modules and other data for the computer 400.

A user may enter commands and information through a user interface 410 or other input devices such as a tablet, electronic digitizer, a microphone, keyboard, and/or pointing device, commonly referred to as mouse, trackball, or touch pad. Other input devices may include a joystick, game pad, satellite dish, scanner, or the like. Additionally, voice inputs, gesture inputs (e.g., via hands or fingers), or other natural user interfaces may also be used with the appropriate input devices, such as a microphone, camera, tablet, touch pad, glove, or other sensor. These and other input devices are often connected to the processing unit 402 through a user interface 410 that is coupled to the system bus 406, but may be connected by other interface and bus structures, such as a parallel port, game port or a universal serial bus (USB). A monitor 412 or other type of display device is also connected to the system bus 406 via an interface, such as a video interface. The monitor 412 may also be integrated with a touch-screen panel or the like.

The computer 400 may operate in a networked or cloud-computing environment using logical connections of a network interface or adapter 414 to one or more remote devices, such as a remote computer. The remote computer may be a personal computer, a server, a router, a network PC, a peer device or other common network node, and typically includes many or all of the elements described above relative to the computer 400. The logical connections depicted in FIG. 4 include one or more local area networks (LAN) and one or more wide area networks (WAN), but may also include other networks. Such networking environments are commonplace in offices, enterprise-wide computer networks, intranets and the Internet.

When used in a networked or cloud-computing environment, the computer 400 may be connected to a public and/or private network through the network interface or adapter 414. In such embodiments, a modem or other means for establishing communications over the network is connected to the system bus 406 via the network interface or adapter 414 or other appropriate mechanism. A wireless networking component including an interface and antenna may be coupled through a suitable device such as an access point or peer computer to a network. In a networked environment, program modules depicted relative to the computer 400, or portions thereof, may be stored in the remote memory storage device.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the disclosure and are thus within the spirit and scope of the present disclosure. From the above description and drawings, it will be understood by those of ordinary skill in the art that the particular embodiments shown and described are for purposes of illustrations only and are not intended to limit the scope of the present disclosure. References to details of particular embodiments are not intended to limit the scope of the disclosure.

What is claimed is:

1. A system comprising:
   one or more computer readable storage media;
   a data store; and
   a recommendation application comprising instructions stored on the one or more computer readable media, wherein the instructions, when executed by one or more computing devices, cause the one or more computing devices to:
   obtain use data indicating a user's interaction, via a graphical user interface (GUI), with a plurality of independent applications included in a platform that is used to clinically treat a health condition of a user, wherein each application of the plurality of independent applications is used to clinically treat the health condition of the user, wherein the instructions cause the one or more computing devices to obtain the use data at least by:
   detecting, in real-time during the user's Interaction with an application of the plurality of independent applications, user input received at the application;
   generating, in real-time during the user's interaction with the application and based on detecting the user input, one or mote events characterizing the user's Interaction with the application; and
   storing, at the data store, the one or more events generated;
   based on the one or more events charactering the user's interaction, identify a pattern of engagement defining the user's engagement, during a specific period of time, with at least one independent application of the plurality of independent applications and identify the user's clinical response to the health condition based on the user's use of the at least one independent application;
based on the pattern of engagement and the user's clinical response to the health condition, identify an independent application used to clinically treat the health condition of the user for integration into the platform; and
automatically integrate, into the platform, the independent application identified.

2. The system of claim 1, wherein the platform generates a graphical user-interface providing access to each independent application of the plurality of independent applications included in the platform and the independent application.

3. The system of claim 1, wherein the pattern of engagement indicates that the user interacts with the at least one independent application most often relative to other independent applications of the plurality of independent applications included in the platform.

4. The system of claim 1, wherein the pattern of engagement comprises at least one feature that corresponds to an aspect of the user's health.

5. The system of claim 4, wherein the instructions, when executed, further cause the one or more computing devices to execute an automated learning algorithm to combine the at least one feature with similar features of an overall user-population.

6. The system of claim 1, wherein the independent application integrated into the platform maximizes an expected outcome of user interactions with the independent application.

7. The system of claim 1, wherein the instructions, when executed, further cause the one or more computing devices to:
access one or more portions of health care information associated with the user;
determine from the health care information accessed, one or more health care concerns associated with the user; and
include the plurality of independent applications in the platform based on the one or more health care concerns determined.

8. A method comprising:
obtaining, using one or more computing devices, use data indicating a user's interaction, via a graphical user interface (GUI), with a plurality of independent applications included in a platform that is used to clinically treat a health condition of a user, wherein each application of the plurality of independent applications is used to clinically treat the health condition of the user, wherein obtaining the use data comprises:
detecting, in real-tune during the user's interaction with an application of the plurality of independent applications, user input received at the application;
generating, in real-time during the user's interaction with the application and based on detecting the user input, one or more events characterising the user's interaction with the application; and
storing, at a data store, the one or more events generated;
based on the one or more events characterizing the user s interaction, identifying, using the one or more computing devices, a pattern of engagement defining the user's engagement, during a specific period of time, with at least one independent application of the plurality of independent applications and identifying the user's clinical response to the health condition based on the user's use of the at least one independent application;
based on the pattern of engagement and the user's clinical response to the health condition, identifying, using the one or more computing devices, an independent application used to clinically treat the health condition of the user for integration into the platform; and
automatically integrating, using the one or more computing devices and into the platform, the independent application identified.

9. The method of claim 8, further comprising generating a graphical user-interface providing access to each independent application of the plurality of independent applications included in the platform and the independent application.

10. The method of claim 8, wherein the pattern of engagement indicates that the user interacts with the at least one independent application most often relative to other independent applications in the plurality of independent applications included in the platform.

11. The method of claim 8, wherein the pattern of engagement comprises at least one feature that corresponds to an aspect of the user's health.

12. The method of claim 11, further comprising executing an automated learning algorithm to combine the at least one feature with similar features of an overall user-population.

13. The method of claim 8, wherein the independent application integrated into the platform maximizes an expected outcome of user interactions with the independent application.

14. The method of claim 8, further comprising:
accessing one or more portions of health care information associated with the user;
determining from the health care information accessed, one or more health care concerns associated with the user; and
including the plurality of independent applications in the platform based on the one or more health care concerns determined.

15. A non-transitory computer readable medium encoded with instructions, the instructions, when executed by one or more computing devices, cause the one or more computing devices to:
obtain use data indicating a user's interaction, via a graphical user interface (GUI), with a plurality of independent applications included in a platform that is used to clinically treat a health condition of a user, wherein each application of the plurality of independent applications is used to clinically treat the health condition of the user, wherein the Instructions cause the one or more computing devices to obtain the use data at least by:
detecting, in real-time during the users interaction with an application of the plurality of independent applications, user input received at the application;
generating, in real-time during the user's interaction with the application and based on detecting the user input, one or more events characterising the user's interaction with the application; and
storing, at a data store, the one or more events generated;
based on the one or more events characterizing the user's interaction, identify a pattern of engagement defining the user's engagement, during a specific period of time, with at least one independent application of the plurality of independent applications and identify the user's clinical response to the health condition based on the user's use of the at least one independent application; and based on the pattern of engagement and the user's clinical response to the health condition, identify, an independent application used to clinically treat the health condition of the user for integration into the platform; and automatically integrate, into the platform, the independent application identified.

16. The non-transitory computer readable medium of claim 15, wherein the instructions, when executed, further cause the one or more computing devices to generate a graphical user-interface providing access to each independent application of the plurality of independent applications included in the platform and the independent application.

17. The non-transitory computer readable medium of claim 15, wherein the pattern of engagement indicates that the user interacts with the at least one independent application most often relative to other independent applications in the plurality of independent applications included in the platform.

18. The non-transitory computer readable medium of claim 15, wherein the pattern of engagement comprises at least one feature that corresponds to an aspect of the user's health.

19. The non-transitory computer readable medium of claim 18, wherein the instructions, when executed, further cause the one or more computing devices to execute an automated learning algorithm to combine the at least one feature with similar features of an overall user-population.

20. The non-transitory computer readable medium of claim 15, wherein the independent application integrated into the platform maximizes an expected outcome of user interactions with the independent application.

21. The non-transitory computer readable medium of claim 15, wherein the instructions, when executed, further cause the one or more computing devices to:
   access one or more portions of health care information associated with the user;
   determine from the health care information accessed, one or more health care concerns associated with the user; and
   include the plurality of independent applications in the platform based on the one or more health care concerns determined.

* * * * *